June 24, 1952 G. MAARSE Plant Pat. 1,108
SYRINGA VULGARIS PLANT
Filed April 21, 1951
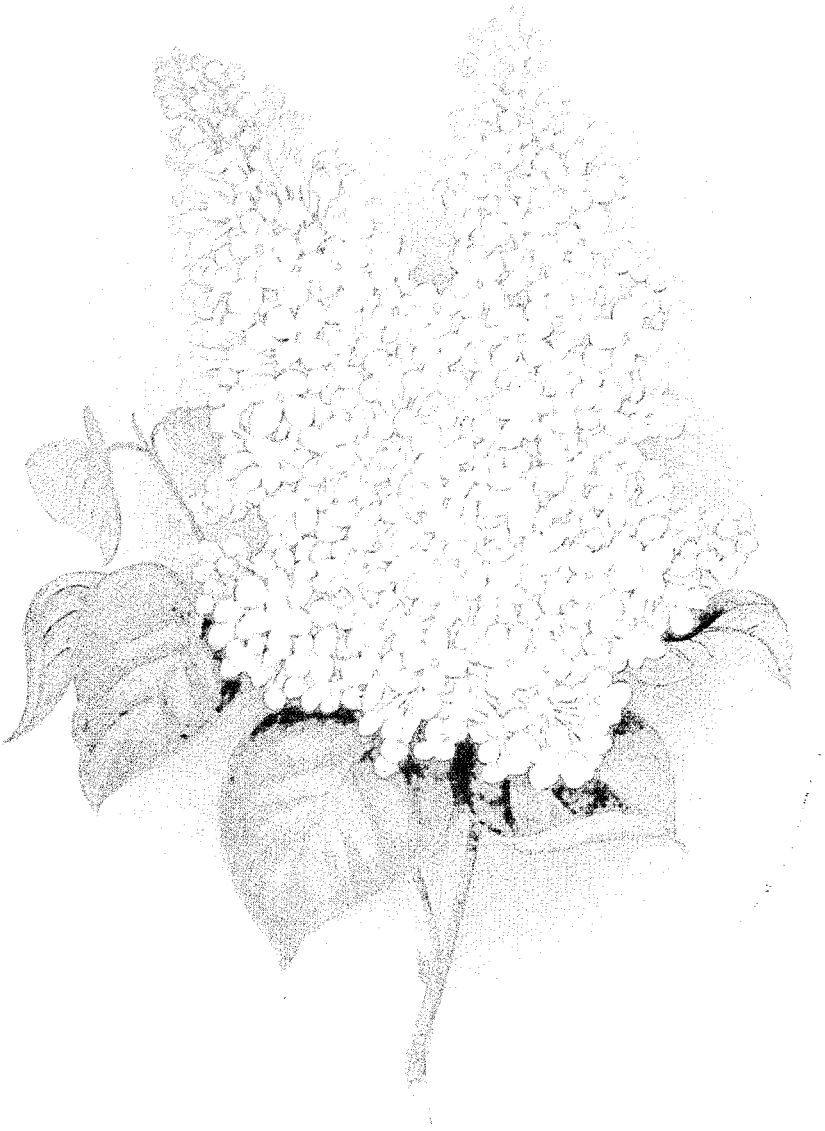
WITNESS
Addison E. Avery
INVENTOR
Gerrit Maarse,
by: John H. Leonard,
His ATTY.

Patented June 24, 1952

Plant Pat. 1,108

UNITED STATES PATENT OFFICE 1,108

SYRINGA VULGARIS PLANT

Gerrit Maarse, Aalsmeer, Netherlands, assignor to Jan Spek, Boskoop, Netherlands Application April 21, 1951, Serial No. 222,201

1 Claim. (Cl. 47—60)

The present discovery relates to a new variety of *Syringa vulgaris*, or lilac, plant.

The new variety originated in my nurseries in Holland as a bud sport or mutation of a French hybrid variety of *Syringa vulgaris* plant which is well known commercially as "Marie Legraye," and not known by me to be patented.

The new variety was asexually reproduced by me at Aalsmeer, Holland, by grafting and its distinguishing characteristics appear to be fixed.

The new variety was asexually reproduced by grafting on ten (10) *Syringa vulgaris* seedlings, the cions from a branch of a *Syringa vulgaris* plant, on which branch had produced blooms showing the mutation in color hereinafter set forth.

The most distinguishing characteristic of the new variety is the unusual color of the inflorescences and of the individual florets.

The drawing illustrates a branch of the new variety, showing the foliage and the inflorescence, the range of tone of the color of the inflorescence and individual florets being indicated in a single inflorescence.

The plant appears to be substantially identical with its parent in growth, size, foliage, hardiness and adaptability, being the usual upright bushy shrub and bearing medium size clusters of relatively large single florets.

It differs radically from its parent in the very unusual color of the inflorescence and individual florets.

The color of the florets just prior to and during opening of the buds is a rather deep yellow, comparable to Maerz and Paul Plate No. 9–L–6. This deeper color fades or changes quite rapidly into a paler and more creamy yellow, ranging generally from Maerz and Paul Pate No. 9–F–1 through 9–J–1, as the florets fully open so that the general tonality of the inflorescence during most of the blooming period ranges from Maerz and Paul Plate No. 9–F–1 through 9–J–1. However, each floret retains its deeper yellow color in the center for a relatively long period despite the paling of the remainder. The buds as well as the florets are relatively large; the leaves are green, comparable to Maerz and Paul Plate No. 21–L–6 and 21–L–7.

The plant forces well under the usual hothouse forcing procedures and conditions used in forcing *Syringa vulgaris* plants, the color of the inflorescence and individual florets being little effected by forcing.

Having thus described my discovery, I claim:

A new and distinct variety of *Syringa vulgaris* plant as described and illustrated, characterized particularly by the yellow coloring of the individual florets and inflorescence.

GERRIT MAARSE.

No references cited.